United States Patent [19]

Mayer et al.

[11] Patent Number: 4,541,011

[45] Date of Patent: Sep. 10, 1985

[54] SYSTEM FOR RECORDING THE LOCATIONS OF WORKPIECE DEFECTS

[75] Inventors: Robert A. Mayer; Michael W. Reith; Jack L. Odell, II, all of Snohomish County, Wash.

[73] Assignee: Western Gear Corporation, Everett, Wash.

[21] Appl. No.: 358,425

[22] Filed: Mar. 15, 1982

[51] Int. Cl.³ .............................................. H04N 7/18
[52] U.S. Cl. .................................... 358/106; 250/563; 356/237
[58] Field of Search ................. 358/101, 106, 107, 97; 356/237, 430, 431; 250/562, 563, 572; 340/707

[56] References Cited

U.S. PATENT DOCUMENTS

| | | | |
|---|---|---|---|
| 3,822,632 | 7/1974 | Chigiotti | 409/139 |
| 3,894,183 | 7/1975 | Barish | 178/18 |
| 3,978,280 | 8/1976 | Kavanagh et al. | 358/93 |
| 4,198,623 | 4/1980 | Misek et al. | 178/18 |
| 4,208,675 | 6/1980 | Bajon et al. | 358/107 |
| 4,295,135 | 10/1981 | Sukonick | 340/731 |
| 4,295,198 | 10/1981 | Copeland et al. | 358/107 |

FOREIGN PATENT DOCUMENTS 52-11086 1/1977 Japan .................................. 356/237

Primary Examiner—Joseph A. Orsino, Jr.
Attorney, Agent, or Firm—Seed and Berry

[57] ABSTRACT

A system for determining and recording the position, size, shape and depth of a defect in a billet or similar workpiece. The workpiece is displayed on the screen of a video display device, and the positions of the defects on the screen are recorded responsive to being manually selected by an operator. In embodiments in which the position of a video camera generating the video image varies with respect to the workpiece, sensors are used to determine the positions of the workpiece with respect to the camera. The position indications from the sensors are applied to a processor which correlates these indications with the position of the defect on the screen to determine the position of the defect on the workpiece.

10 Claims, 3 Drawing Figures

SYSTEM FOR RECORDING THE LOCATIONS OF WORKPIECE DEFECTS

DESCRIPTION

TECHNICAL FIELD

This invention relates to workpiece finishing equipment and, more particularly, to a system for generating a record of the location and estimated depth of defects on billets and other similar workpieces.

BACKGROUND ART

Billets emerging from a steel mill typically have a surface layer of imperfections or scale, as well as a number of spaced-apart, fairly deep cracks. If the billets are sent directly to a rolling mill, the defects are reproduced in the finished product. Consequently, the surface layer or scale is removed from the billets in a "skinning" procedure in which the billet reciprocates beneath a grinding wheel which removes a thin layer from the surface of the billet. Modern skinning machines operate automatically, with the grinding wheel automatically reciprocating between the ends of the billet and the grinding wheel pressure being automatically adjusted.

After the automatic skinning procedure has been completed, the cracks and deep imperfections remain. These defects are normally manually removed with a grinding wheel in a procedure known as "spotting."

Attempts have been made to automate the spotting procedure in the same manner as the skinning procedure. However, skinning of the billet is uniform about the entire surface of the billet. The skinning procedure thus lends itself to automation. Unlike the skinning procedure, the spotting procedure introduces a number of random variables, such as the location, size, shape and depth of the defects. These random variables have heretofore prevented the automatic spotting of billets and the like.

Prior attempts to design automatic spotting machines have generally used magnetic or optical flaw detectors having a known position in relation to the billet to generate a record of the location of all defects on the billet. The record may then be used by an automatic grinding machine to grind each of the defects. Alternatively, the position of the defects may be entered by manual means in order to control the operation of a grinder such as disclosed in U.S. Pat. No. 3,822,632.

These previous attempts to determine the locations of defects have generally not been successful because it is difficult for the sensors to accurately determine the depth of the defect as well as its size and shape, particularly when the shape of the defect is geometrically complex. As a result, information concerning the defect must be entered manually; but no system has been devised for allowing such information to be easily and quickly entered by manual means. Furthermore, other manual defect entry devices allow only the location of the defect to be entered, but not their size, shape and depth.

DISCLOSURE OF THE INVENTION

It is an object of the invention to provide a system for easily and quickly recording the position of defects on a billet.

It is another object of the invention to provide a billet defect entry system which is also capable of accurately recording the size and shape of each defect.

It is still another object of the invention to provide a billet defect entry system which records the depth of each defect as its position is recorded.

It is a further object of the invention to provide a defect entry system which may easily interface with an automatic grinding machine.

It is a still further object of the invention to provide a defect entry system which may be implemented using a variety of techniques.

These and other objects of the invention are provided by a video camera generating an image of the workpiece and displaying it on the screen of a video display device. The location of the camera with respect to the workpiece is fixed so that the position of the defect on the screen of the display device corresponds to the position of the defect on the workpiece. Various embodiments of marking devices generate an electrical signal indicative of the location of the defect on the screen of the display device, which is received by a processor which records the position of the defect on the workpiece. In one embodiment, the marking system may be a conventional light pen which records the position of the light pen on the screen of the video display device. An operator utilizes the light pen to trace a line over the defect, and the locations of the light pen on the screen are recorded as a record of the size, shape and location of the defect. Alternatively, the marking device may be a switch matrix formed on a transparent overlay positioned on the screen or an array of light-emitting devices and sensors positioned along the edges of the screen. In any case, by recording information concerning the defect as it appears on the screen of the video display device, the information is easily and quickly entered to create a complete record of defects for the billet. A manual entry device is also provided to generate an indication of the depth of each defect, which is recorded along with the other information concerning the defect. The image generated by the video camera may cover a variable area of the workpiece, in which case a signal proportional thereto is used to scale the location of the defects on the screen of the video display device. The size of the workpiece surface that is imaged may be varied by either moving the camera toward and away from the workpiece or by utilizing a video camera having a zoom lens. In many cases, the workpiece is greatly elongated, thus making it difficult to image the entire length of the workpiece. Under these circumstances, the workpiece may be mounted on a car that moves along a track extending along the longitudinal axis of the workpiece. The position of the car is then recorded so that it can be correlated to the position of the defect on the screen of the video display device in order to determine the position of the defect on a workpiece. Similarly, where the workpiece is too wide to be imaged by the camera, the camera may be moved transversely across the workpiece. The position of the camera is then recorded so that it can be correlated with the position of the defect on the screen of the video display device to determine the position of the defect on the workpiece.

BEST MODE FOR CARRYING OUT THE INVENTION

Figure 1:
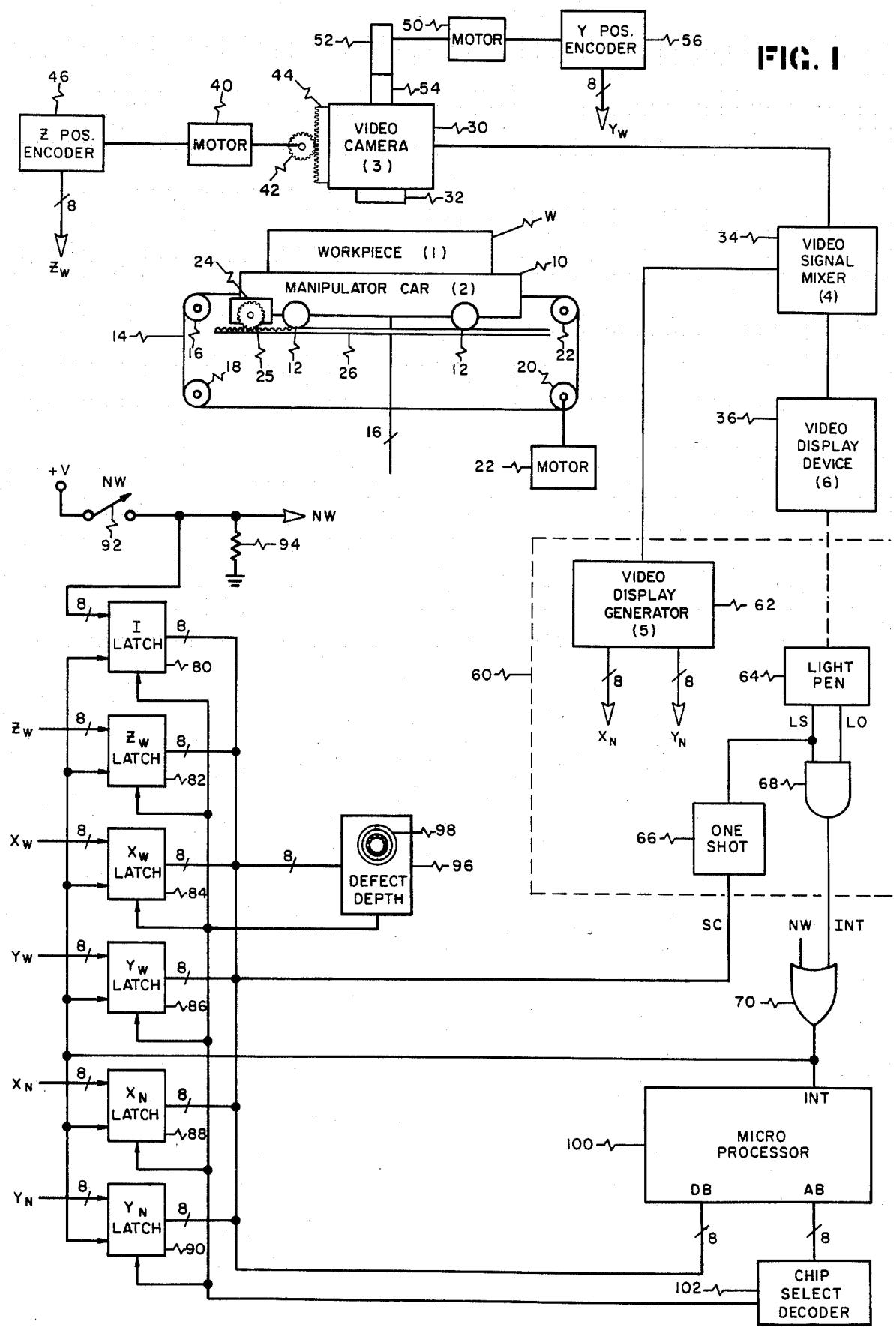
FIG. 1 is a schematic of one embodiment of the defect entry system.

One embodiment of the inventive defect entry system, as illustrated in FIG. 1, includes a manipulator car 10 carrying a workpiece W, such as a billet, ingot, or the like. The manipulator car 10 is supported on a surface by wheels 12, and it is propelled in opposite directions by a cable 14 which engages a series of sheaves 16, 18, 20, 22. One of the sheaves 20 is driven by a conventional bidirectional motor 22 which may be either electric or hydraulic. A digital encoder 24 is mounted on the car 10. The encoder 24 is driven by a shaft-mounted gear 25 which meshes with a fixed rack 26. The encoder 24 contains internal gearing so that its output $X_w$ indicates the position of the car 10, although the shaft of the encoder 24 rotates throughout a large number of revolutions. The sixteen-bit digital output $X_w$ from the encoder 24 thus identifies the position of the manipulator car 10, which is a measure of the longitudinal or X axis position of the workpiece W in a fixed frame of reference. It will be understood that other systems for longitudinally moving the workpiece and providing a signal indicative of the workpiece's position may be used. For example, the motor 22 could be mounted on the car 10, and a gear mounted on the shaft of the motor 22 could mesh with the rack 26. Also, the workpiece W can remain stationary where the field of view of the camera 30 is greater than the length of the workpiece W.

A conventional video camera 30 is mounted above the workpiece W with its lens 32 focused on either a portion or all of the surface of the workpiece W, which is being examined for defects. The video signal from the camera 30 passes through a conventional video signal mixer 34 and is received by a conventional video monitor 36. The video monitor 36 displays at least a portion of the surface of the workpiece W with sufficient clarity to easily spot defects in the surface of the workpiece W.

The field of view of the camera 30 in a direction transverse to the longitudinal axis of the workpiece W is generally sufficiently large to image the entire width of relatively narrow workpieces. However, relatively wide workpieces may require that the position of the video camera 30 with respect to the workpiece W be adjusted in order to image the entire width of the workpiece W. Accordingly, the position of the video camera 30 may be adjusted toward or away from the workpiece W in order to increase the area of the workpiece being viewed by the camera since the camera has a diverging viewing angle. The same effect may be achieved by using a camera 30 having a zoom lens actuated by a motor. Alternatively, the position of the video camera may be adjusted in a direction transverse to the longitudinal axis of the workpiece W in order to view different portions of the workpiece W. The camera 30 is moved vertically toward and away from the workpiece W by actuating a conventional motor 40 in either direction. The shaft of the motor 40 is connected to a pinion gear 42 which meshes with a rack 44 mounted along the side of the camera 30. The shaft of the motor 30 is also connected to a conventional position encoder 46 which generates an eight-bit digital word indicative of the vertical position of the camera 30. A zoom lens mounted on the camera 30, as described above, would be actuated by the motor 40 so that the encoder 46 would similarly indicate the viewing area of the camera.

The camera 30 is moved transversely in a horizontal plane by energizing a second motor 50 in either direction. The shaft of the motor 50, like the shaft of motor 40, is connected to a pinion gear 52 which meshes with a rack 54 mounted on the upper surface of the camera 30. The shaft of the motor 50 also drives a conventional encoder 56 which generates a digital output indicative of the transverse position of the camera 30. Other actuating systems and position-measuring devices may also be used to provide electrical signals indicative of the transverse and vertical positions of the camera 30.

As mentioned above, the purpose of the defect entry system is to identify the location and size of defects on the surface of the workpiece W. Accordingly, a workpiece position-identifying circuit 60 is used to provide digital words $X_n$, $Y_n$ indicative of the X and Y positions, respectively, on the video monitor 36 of the image of a defect of the workpiece surface. The position-identifying system 60 includes a conventional video display generator 62 which basically provides an output to the video signal mixer 34 of a single spot scanning the screen of the video monitor 36 line by line from top to bottom and each line of the video screen from left to right. The video display generator 62 generates outputs $X_n$, $Y_n$ indicative of the position of the spot being output to the video signal mixer 34. A conventional light pen 64 placed on the screen of the video monitor 36 detects the spot when the spot reaches the area of the screen which the light pen 64 is contacting and generates a pulse on the light output (LO) line of the light pen 64. At that time, the position outputs $X_n$, $Y_n$ identify the position of the spot and hence the position of the light pen 64 on the screen of the video monitor 36. The light pen 64 includes an internal switch (not shown) which is manually actuated by the machine operator when the light pen is being used to identify a defect. Closing of the lightswitch generates a logic "1" on the lightswitch (LS) output of the light pen 64.

The lightswitch output of the light pen 64 is connected to a one-shot 66 which generates a short pulse when the lightswitch is initially closed. As explained in greater detail hereinafter, the pulse at the output of the oneshot 66 indicates that the position of a new defect is being identified. The lightswitch output LS of the light pen 64 is applied to an AND gate 68 which gates the light output pulses from the light pen 64 to OR gate 70 each time the light pen detects the scanning spot when the lightswitch is closed. A pulse is thus generated at the output of the AND gate 68 each time the digital words $X_n$, $Y_n$ identify the X and Y positions, respectively, of the light pen 64 on the screen of the video monitor 36 as long as the lightswitch of the light pen 64 is closed. Additionally, a pulse is produced by the one-shot 66 when the lightswitch in the pen 64 is initially closed.

The remainder of the system illustrated in FIG. 1 processes the data from the defect position-identifying system 60 and calculates the position and size of the defect on the workpiece W by comparing the position of the defect on the video monitor screen and the position of the workpiece W with respect to the video camera 30. Each time a pulse is produced by OR gate 70, a number of latches 80, 82, 84, 86, 88, 90 are triggered to store digital words which are being applied to their respective inputs. Thus latch 82 stores a signal indicative of the vertical position of the camera 30, latch 84 stores a signal indicative of the longitudinal position of the workpiece, and latch 86 stores a signal indicative of the transverse position of the camera 30. It will be remembered that a pulse is generated by OR gate 70 when the outputs of the video display generator 62 identify the position of the light pen on the screen of the video monitor 36. Accordingly, when latch 88 is triggered, it receives a signal indicative of the position of the light pen in the horizontal or X direction, and latch 90, when triggered, receives a signal indicative of the position of the light pen in the vertical or Y direction.

The system also includes a conventional data entry device 96 having an adjustment knob 98 connected to an internal digital encoder which generates a digital output indicative of the position of the knob 98. The entry device is used to enter information into the system indicative of the operator's estimate of the relative depth of the defects on the workpiece surface.

The entire system is reset upon starting to examine a new workpiece by closing a new workpiece switch 92, thereby applying a logic "1" to the NW output, which is normally held low through resistor 94. The NW output is also applied to an input of OR gate 70 in order to trigger all of the latches 80–90. Thus, if latch 80 is triggered by closing switch 92, the low-order bit of the latch 80 input receives a logic "1." If, however, the latches 80–90 are triggered by the output of the AND gate 68, the low-order bit of latch 80 receives a logic "0." The condition of the latch 80 thus indicates whether the data in latches 82–96 indicates either the initial position of the workpiece W or a subsequent position after the workpiece has been moved. Thus, actuating switch 92 allows the position of the car 10 to be correlated to the position of the workpiece W in the field of view of the video camera 30. The system could also be initialized by another drive, such as an automatic spotting device, which has recorded the position of the workpiece W as a function of the car position.

The output of OR gate 70 is also applied to an input of a conventional microprocessor 100 operating in accordance with a set of instructions explained in greater detail hereinafter. Basically, the microprocessor 100 sequentially examines the outputs of each latch 80–90 when a pulse is received from the output of OR gate 70. A pulse is generated by OR gate 70 when either the new workpiece switch 92 is closed or the scanning spot is detected by the light pen 64 when the internal lightswitch is closed. The processing unit, then, first reads appropriate inputs by gating the contents of latches 80–90 and entry device 96 onto the data bus one at a time as determined by a chip-select decoder 102 from the address bus. The microprocessor then performs the necessary calculations to determine a point on a line circumscribing a defect, and stores the location of the point for subsequent readout.

Figure 2:
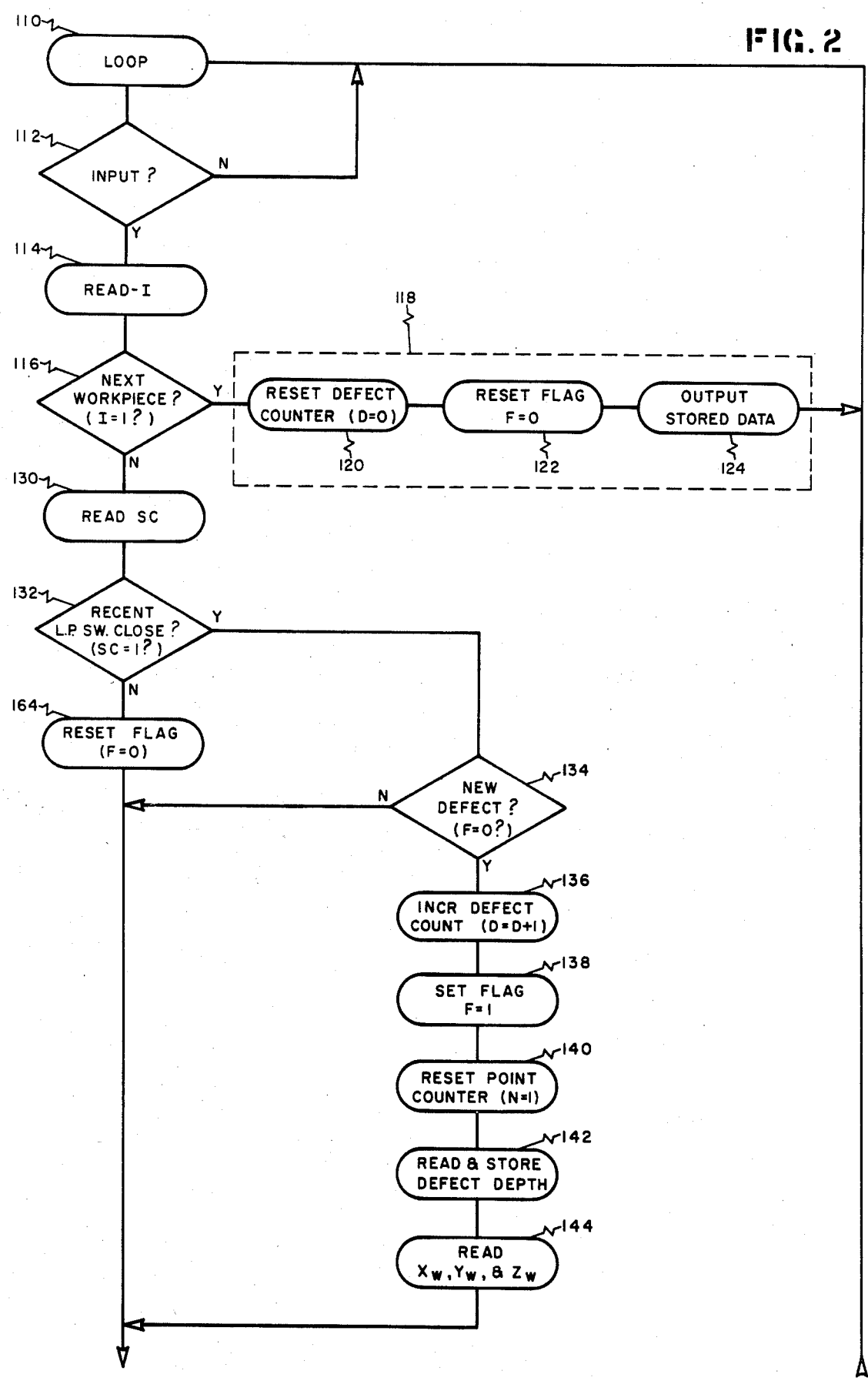
FIG. 2 is a flow chart of the software for controlling the operation of the embodiment of FIG. 1.
Figure 2:
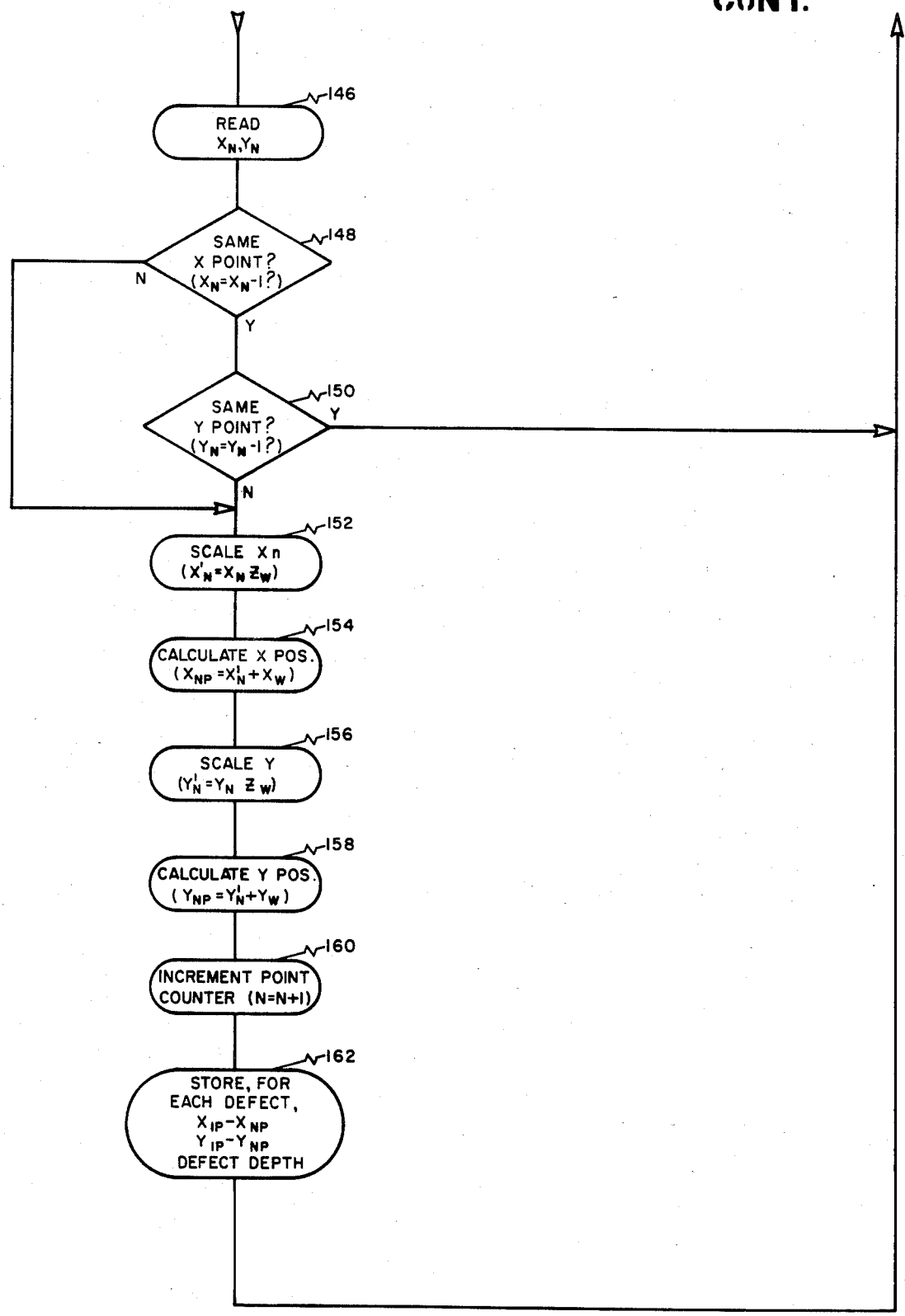

A flow chart of the program for controlling the operation of the microprocessor 100 is illustrated in FIG. 2. After the microprocesor 100 has been initialized, it continuously loops at 110 while periodically checking for an input from OR gate 70. When an input occurs, either because the new workpiece switch 92 has been closed or the light pen 64 has detected the scanning spot, the program exits the loop and the data in latch 80 is read onto the data bus by the chip-select decoder 102. It will be remembered that the low-order bit from latch 80 is "1" if the trigger input from OR gate 70 is caused by closure of the new workpiece switch 92. Accordingly, the program determines at 116 that the contents "I" of the latch 80 is "1" and branches to a new workpiece loop 118. In the new workpiece loop 118, a defect counter is reset to zero at 120, a flag (provided for a purpose explained hereinafter) is reset to zero at 122, and the data identifying the size and location of the defects for the previous billet is gated to an output port at 124. The program then returns to the loop 110 to monitor the trigger input.

The light pen 64 is then applied to the screen of the video monitor 36 and the lightswitch is closed. A short time thereafter, the light pen 64 detects the scanning spot, thereby applying a pulse to the trigger input of the processor 100. The program then reads "I" (the contents of latch 80), and, since "I" is now "0," branches from 116 to 130, where SC (the output of one-shot 66) is read on the low-order bit of the data bus. The duration of the output from one-shot 166 is longer than the scanning time of the spot throughout the entire screen so that the low-order bit of the data bus is high for at least the first trigger pulse of the microprocessor. Accordingly, the program determines that the low-order bit of the data bus is high at 132 and branches to 134, where the condition of the flag is examined. It will be remembered that the flag was reset to zero at 122 while the program was executing the new workpiece loop 118. Accordingly, the program branches from 134 to 136, where the defect counter is incremented. The flag is then set to one at 138, the point counter is reset to one at 140, the estimated defect depth signal is read from data entry device 86 and stored at 142, and the position of the workpiece $X_w$ and position of the video camera $Y_w$ and $Z_w$ are read at 144. The digital outputs $X_w$, $Y_w$ and $Z_w$ are read from the latches 84, 86, 82, respectively, by the chip-select decoder 102 from the address bus of the microprocessor 100. The flag is thus reset at 122 to cause the program to progress through steps 136–144 upon the first interrupt after the internal switch of the light pen 64 has been closed in order to initialize certain variables, to read and store a signal indicative of the estimated depth of the defect, and to read the position of the workpiece W with respect to the video camera 30. The flag is then set at 138 so that steps 136–144 are bypassed until the lightswitch in the pen 64 is once again closed when the position of a new defect is being entered.

Each time a trigger input occurs, the X and Y positions of the light pen 64 are read at 146, and the program tests at 148 to determine whether the new X position of the pen is the same as the previous position. If the positions are the same, the program tests at 150 whether the Y position is the same as the previous Y position. If so, the program returns to the loop 110 insofar as it is not desirable to fill memory with duplicates of the same point. Assuming that either the new X point is different from the previous X point or the new Y point is different from the previous Y point, the program branches to 152. At 152, the X position of the defect on the workpiece W, as represented by its position on the video screen, is scaled by multiplying the position on the screen $X_n$ by the vertical position the video camera 30. Since the size of the image viewed by the video camera 30 is a function of the distance between the camera 30 and the object being viewed, the actual position of the object away from a center axis of the camera 30 is proportional to the position of the object on the screen and the distance between the camera and the object. The actual position of the point on the workpiece corresponding to the location of the light pen is thus proportional to the distance between the video camera 30 and the workpiece W. The actual position of the defect on the workpiece identified by the light pen is then calculated at 154 by adding the scaled position of the light pen $X_n'$ to the longitudinal position of the workpiece $X_w$. The position of the light pen in the Y direction is then scaled at 156, and the Y position of the defect on the workpiece is calculated at 158 by adding the scaled Y position $Y_n'$ to the tranverse position of the video camera 30 in a horizontal plane. It will be understood, however, that for relatively narrow workpieces W, the camera 30 may remain fixed, thereby making it unnecessary to process steps 152-158.

The program then progresses to 160, where the point counter is incremented and the actual X and Y position for each point of a line circumscribing the defect, as well as the estimated defect depth, is stored at 162. Finally, the program returns to the loop 110 and awaits another trigger pulse applied to its input.

On the next pass of the scanning spot, the microprocessor 100 is once again triggered and the program branches to 132 in the same manner as explained above. Depending upon the duration of the pulse from the one-shot 66, SC may be either "1" or "0." Assuming that SC is still "1," the program branches to 134, where the value of the flag is tested. Since the flag was previously set to one at 138, the program branches from 134 directly to 146 and then reads and calculates the actual position of the next point along a line circumscribing the defect. Upon the next trigger pulse, the program once again progresses to 132. Assuming that the output of one-shot 66 is now "0," the program branches from 132 to 164. At 164, the flag is reset to zero before progressing to 146, where the contents of latches 88 and 90 are read. Since the flag has been reset to zero at 164, the next time the light pen switch is closed subsequent to being opened, the program branches from 132 to steps 134-144. The light pen switch is thus closed for each defect.

The essence of the invention is the display of a workpiece surface, identification of the location of defects on the displayed surface, and correlating the displayed positions with the actual position of the defects on the workpiece surface. Consequently, the location of the defects on the displayed surface can be input with a variety of systems in addition to the light pen system described above. For example, the defect position-identifying system 200 of FIG. 3 may replace the defect-identifying system 60 of FIG. 1. Basically, the defect-identifying system 200 utilizes the same video monitor 36 as in FIG. 1, although the signal from the video camera 30 may be applied directly to the monitor 36 since the video signal mixer 34 is not required. Basically, an X-Y data input device 201 is used to determine the position of a pointer or similar instrument on the video display screen. In one embodiment, the X-Y data input device 201 may include a number of light-emitting diodes and light sensors arranged on the periphery of the video screen so that when a pointer is placed on the screen, light extending from a light-emitting diode on one vertical edge of the screen to one of the sensors extending along the other vertical edge of the screen is broken. The particular sensor no longer receiving light thus identifies the X position of the pointer. In the same manner, light-emitting diodes and light sensors extending along opposite vertical edges of the display screen identify the Y position of the pointer. The output of each of the horizontally positioned light sensors is applied to the inputs of an encoder 202 while the output of each of the light sensors extending along the vertical edge are applied to the Y encoder 204. The encoders 202, 204 generate a binary signal indicative of which light sensor is not receiving light from its corresponding LED. Each output from the X encoder 202 is connected to the anode of a respective diode (indicated generally at 206) so that the line connected to the cathodes goes high if any of the outputs go high. Thus, as soon as the pointer is applied to the screen, the input to one-shot 208, which is normally held low through resistor 210, goes high, causing a pulse to be applied to one input of OR gate 212. At the same time, the pulse is applied to the SC output and is processed in the same manner as the pulse from one-shot 66 of FIG. 1. In other words, the SC pulse is produced when the first point is selected of a line circumscribing each defect.

Figure 3:
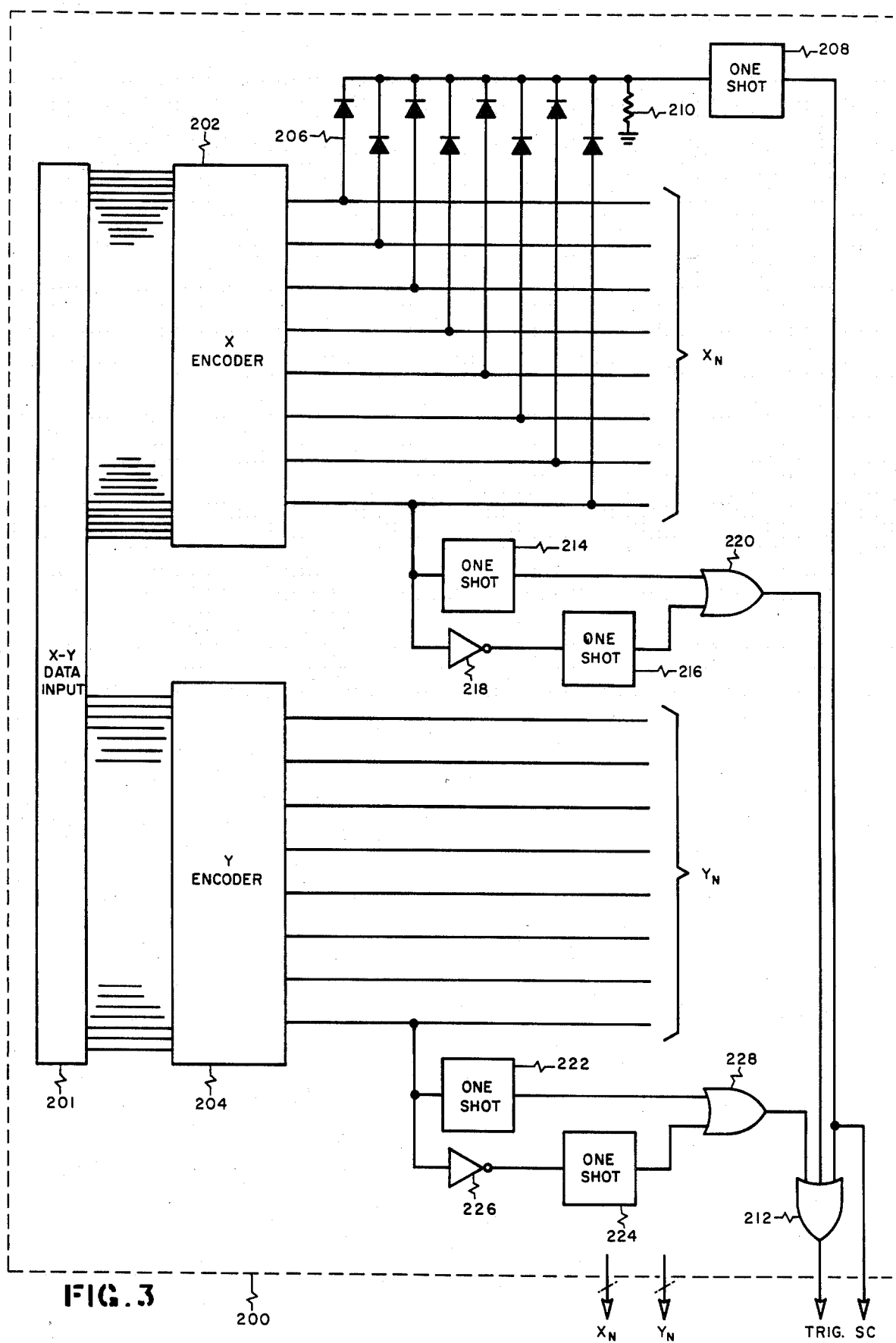
FIG. 3 is a schematic of an alternative embodiment of the defect entry position system.

Although an X-Y data entry device 201 using diodes has been suggested for use with the embodiment of FIG. 3, it will be understood that other X-Y data input devices 201 may also be used. For example, the X-Y data input device 201 may be a commercially available X-Y switch matrix. This device includes a transparent overlay containing conductive switches in a matrix arrangement. The overlay covers the screen of the video display device 36 so that touching the screen closes the switch contacts at that location on the screen.

The low-order bit of the X encoder 202 is applied to a one-shot 214 and to a second one-shot 216 through an inverter 218. The outputs of both one-shots 214, 216 are then applied to an OR gate 220. One-shot 214 is triggered on the low-to-high transition of the low-order bit of the encoder output while one-shot 216 is triggered on the high-to-low transition of the low-order bit of encoder 202. OR gate 220 produces a pulse whenever either one-shot 214 or one-shot 216 is triggered. As the pointer is moved across the screen, the light reaching the light sensors is sequentially interrupted so that the output of encoder 202 increments one digit at a time. Consequently, each time a different sensor in the horizontal array of sensors is interrupted, the low-order bit from the encoder 202 changes, thereby triggering one of the one-shots 214, 216 and causing a pulse to be generated at the output of OR gate 220.

In a similar manner, the low-order bit from the Y encoder 204 is applied to a first one-shot 222 and to a second one-shot 224 through inverter 226. The outputs of both one-shots 222, 224 are applied to an OR gate 228 so that the OR gate 228 produces a pulse each time the low-order bit from the Y encoder 204 changes. The respective outputs from OR gates 220, 228 are applied to OR gate 212 so that the microprocessor 100 is triggered each time the pointer moves to a new location. The output of one-shot 208 is also applied to OR gate 212 in case the initial X and Y position of the pointer causes the low-order bit of both the X and Y encoders 202, 204 to remain low.

The defect position-identifying system 200 of FIG. 3 thus operates in the same manner as the defect position-identifying system 60 of FIG. 1. The microprocessor 100 is triggered each time a new X or Y position of a point on a line circumscribing or tracing over the defect is selected. Digital signals identifying the X and Y positions so selected are then recorded by the latches 88, 90, respectively. Additionally, as the first point for each defect is selected, an SC pulse is generated which is detected by the microprocessor 100 in the program step 132 of FIG. 2 to cause the program to proceed through steps 134-144 each time a new defect is selected.

Although the embodiments of the invention which have been described herein record the points for a line circumscribing or tracing over the defect, the position and size of a defect may be recorded in a different manner. For example, light pen 64 may be used to merely record the location of the defect, and data indicative of the size of the billet may be entered separately. Also, a variety of systems may be used to enter data in connection with the screen of the video monitor 36. For example, a manually adjustable "joystick" may be used to move a cursor on the video screen around a defect in order to enter the defect's size and position.

We claim:

1. A system for providing a record of the location of visually perceptible defects on the surface of a workpiece, comprising:
    a video camera generating an image of said workpiece surface, said camera having a known position with respect to said workpiece;
    video display means receiving the output of said video camera for displaying said image on a video screen;
    marking means for providing an electrical indication of the position of said visually perceptible defects on the screen of said video display means;
    processing means receiving the electrical indications from said marking means to determine and record the position of said defect on the surface of said workpiece by correlating the position of the defect as viewed on said video display means with the position of said video camera with respect to said workpiece;
    actuating means for changing the relative positions of said video camera and said workpiece in at least one dimension substantially parallel to the surface of said workpiece; and
    position-sensing means for providing an electrical indication of the position of said workpiece with respect to said video camera in each dimension of workpiece movement, said position indication being applied to said processing means which correlates the relative position between said workpiece and camera with the position of said defect on the screen of said video display means to determine and record the position of said defect on the surface of said workpiece as the relative position between said workpiece and camera changes.

2. The system of claim 1 wherein said marking means comprise a light pen adapted for placement on said video screen at a point to be marked, said light pen generating an output when the scan of said video screen reaches the point on said video screen that said light pen is contacting, video display generator means for providing a light pen position indication of the location of said video screen currently being scanned, and latch means connected to said display generator means and said light pen for recording a video scan location indication responsive to an output from said light pen, thereby identifying the location of said light pen.

3. The system of claim 1 wherein said marking means comprise:
    a first row of light-emitting devices positioned along one edge of said video screen;
    a first row of light-detecting devices positioned along an edge of said video screen opposite the row occupied by said first row of light-emitting devices so that said first row of light-detecting devices receives light from said first row of light-emitting devices when the path therebetween is unobstructed;
    first decoder means connected to said first row of light-detecting devices for providing an indication of any light-detecting devices in said first row not receiving light from said first row of light-emitting devices, thereby providing an indication in one dimension of the location of a light-obstructing indicator on said screen;
    a second row of light-emitting devices positioned along an edge of said video screen perpendicular to the rows occupied by said first light-emitting devices and said first light-detecting devices;
    a second row of light-detecting devices positioned along an edge of said video screen opposite the row occupied by said second row of light-emitting devices so that said second row of light-detecting devices receives light from said second row of light-emitting devices when the path therebetween is unobstructed; and
    second decoder means connected to said second row of light-detecting devices for providing an indication of any light-detecting device in said second row not receiving light from said second row of light-emitting devices, thereby providing an indication in one dimension of the location of said light-obstructing indicator on said screen, whereby electrical indications of the position of a defect on a workpiece displayed on said screen are provided by said decoder means responsive to pointing to said defect with said light-obstructing indicator.

4. The system of claim 1 wherein said marking means comprise:
    a switch matrix overlay having a plurality of isolated row conductors and a plurality of isolated column conductors embedded in a transparent sheet in a manner that permits a predetermined row conductor and a predetermined column conductor to contact each other at a location in which pressure is applied to said overlay, said overlay being positioned on the screen of said video display to identify the location of a defect on the surface of said workpiece as displayed on said video display; and
    decoder means connected to said row and column conductors for providing an indication of the location of the contact between said row and column conductors, thereby providing an electrical indication of the position of a defect on the workpiece as displayed on the screen of said video display means.

5. The system of claim 1, further including manual entry means for providing an electrical indication of the depth of each defect and wherein said processing means receives and records said electrical depth indications each time the position of the corresponding defect is recorded.

6. A system for providing a record of the location of visually perceptible defects on the surface of a workpiece, comprising:
    a video camera generating an image of said workpiece surface, said camera having a known position with respect to said workpiece;
    video display means receiving the output of said video camera for displaying said image on a video screen;

marking means for providing an electrical indication of the position of said visually perceptible defects on the screen of said video display means;

processing means receiving the electrical indications from said marking means to determine and record the position of said defect on the surface of said workpiece by correlating the position of the defect as viewed on said video display means with the position of said video camers with respect to said workpiece;

scaling means for varying the size of the workpiece surface displayed by said video camera image; and sensing means for providing an electrical scaling indication proportional to the size of the workpiece surface covered by said video camera image, said scaling indication being applied to said processing means which scales the electrical indication from said marking means by multiplying the defect position indication from said marking means by a scale factor derived from the electrical scaling indication generated by said sensing means.

7. The system of claim 6 wherein said video camera has a field of view which changes with the distance between said camera and workpiece, and wherein said scaling means includes camera-actuating means for selectively moving said video camera toward and away from said workpiece, and camera position-sensing means for providing, as said electrical scaling indication, an indication of the position of said camera toward and away from said workpiece.

8. A system for providing a record of the location of visually perceptible defects on the surface of an elongated workpiece, comprising:

a video camera generating an image of said workpiece surface, said camera having a known position with respect to said workpiece;

video display means receiving the output of said video camera for displaying said image on a video screen;

marking means for providing an electrical indication of the position of said visually perceptible defects on the screen of said video display means;

a car supporting said workpiece, said car being positioned on a track aligned with the longitudinal axis of said workpiece;

car-actuating means for selectively moving said car along said track;

car position-detecting means for providing an electrical indication of the position of said car;

camera-actuating means for selectively moving said video camera along an axis perpendicular to the longitudinal axis of said workpiece;

camera position-detecting means for providing an electrical indication of the position of said camera; and processing means receiving the electrical indications from said marking means, said car position-detecting means and said camera position-detecting means to determine and record the position of said defect on the surface of said workpiece and determine the position of said workpiece with respect to said camera and correlate said position determination with the position of said defect on the screen of said video display to determine the position of said defect on the surface of said workpiece.

9. The system of claim 8, further including scaling means for varying the size of the workpiece surface covered by said video camera image, and sensing means for providing an electrical scaling indication proportional to the size of the workpiece surface covered by said video camera image, said electrical scaling indication being received by said processing means which scales the electrical indications from said marking means and said camera position-detecting means by multiplying said defect position indication and said camera position indication by a scale factor derived from the electrical scaling indication generated by said sensing means.

10. The system of claim 9 wherein said marking means comprise a light pen adapted for placement on said video screen at a point to be marked, said light pen generating an output when the scan of said video screen reaches the point on said video screen that said light pen is contacting, video display generator means for providing an indication of the location of said video screen currently being scanned, and respective latch means receiving a video scan position indication, said car position indication, said camera position indication, and said scaling indication, said latch means being triggered by the output of said light pen for recording said indications responsive thereto.

* * * * *